United States Patent
Cordero et al.

(10) Patent No.: US 6,434,410 B1
(45) Date of Patent: Aug. 13, 2002

(54) ELECTRODE FOR MEASURING ELECTROPHYSIOLOGICAL SIGNALS USING LIQUID ELECTROLYTIC GEL WITH A HIGH SALT CONCENTRATION

(75) Inventors: Rafael M. Cordero, Tewksbury; Philip H. Devlin, Brookline, both of MA (US)

(73) Assignee: Aspect Medical Systems, Inc., Newton, MA (US)

( * ) Notice: Subject to any disclaimer, the term of this patent is extended or adjusted under 35 U.S.C. 154(b) by 0 days.

(21) Appl. No.: 09/100,290

(22) Filed: Jun. 19, 1998

(51) Int. Cl.[7] .................................................. A61B 5/04
(52) U.S. Cl. ........................ 600/396; 600/391; 600/395
(58) Field of Search ................................ 600/391, 392, 600/394, 395, 396, 397; 607/149, 52, 153

(56) References Cited

U.S. PATENT DOCUMENTS

| | | | | |
|---|---|---|---|---|
| 4,362,165 A | * | 12/1982 | Carmon et al. | 600/396 |
| 4,370,984 A | * | 2/1983 | Cartmell | 600/385 |
| 4,516,581 A | * | 5/1985 | Sessions | 600/396 |
| 4,522,211 A | * | 6/1985 | Bare et al. | 600/392 |
| 4,570,637 A | * | 2/1986 | Gomes et al. | 600/395 |
| 4,736,752 A | * | 4/1988 | Munck et al. | 607/152 |
| 4,852,571 A | * | 8/1989 | Gadsby et al. | 600/396 |
| 5,352,315 A | * | 10/1994 | Carrier et al. | 156/267 |
| 5,406,945 A | * | 4/1995 | Riazzi et al. | 600/394 |
| 5,427,096 A | * | 6/1995 | Bogusiewicz et al. | 600/396 |
| 5,465,715 A | * | 11/1995 | Lyons | 600/391 |
| 5,565,143 A | * | 10/1996 | Chan | 252/514 |
| 5,566,672 A | * | 10/1996 | Faasse, Jr. | 600/372 |
| 5,622,168 A | * | 4/1997 | Keusch et al. | 600/391 |
| 5,707,502 A | * | 1/1998 | McCaffrey | 204/403 |
| 5,785,040 A | * | 7/1998 | Axelgaard | 600/391 |
| 5,855,820 A | * | 1/1999 | Chan et al. | 252/511 |

FOREIGN PATENT DOCUMENTS

| | | |
|---|---|---|
| EP | 0 619 094 | 10/1994 |
| EP | 0 627 193 | 12/1994 |
| WO | WO 81 01646 | 6/1981 |

* cited by examiner

Primary Examiner—John P. Leubecker
Assistant Examiner—Brad C. Blaise
(74) Attorney, Agent, or Firm—Hale and Dorr LLP

(57) ABSTRACT

An electrophysiological electrode includes multiple layers of materials to isolate liquid electrolytic gels from the conductive inks on the flexible circuit of the electrode substrate. Such an electrode has a much longer shelf life under normal storage conditions than other electrodes of such construction with high salt content liquid electrolytic gel, and is able to maintain acceptable impedance upon its eventual use.

15 Claims, 6 Drawing Sheets

ELECTRODE FOR MEASURING ELECTROPHYSIOLOGICAL SIGNALS USING LIQUID ELECTROLYTIC GEL WITH A HIGH SALT CONCENTRATION

BACKGROUND OF THE INVENTION

Electrodes which are used to record biopotentials from the surface of the skin generally require the use of a conductive liquid or solid gel to provide a continuous conductive path between the recording surface (i.e., the skin) and the electrode sensing element. Conductive gels contain a salt (KCl or NaCl) in order to achieve electrical current flow. The preferred gel is one with a high salt content, since such a gel produces a better conductor than that obtained when using a gel with a low salt content. In addition, the use of a high salt content gel typically requires less skin abrasion at the time of application to reduce the impedance of the skin-electrode interface after subsequent electrode application.

For ease of use, it is desirable to apply the conductive liquid or solid gel at the point of manufacture, creating a "pre-gelled" electrode. U.S. Pat. No. 4,559,950 issued to Vaughn and U.S. Pat. No. 5,309,909 issued to Gadsby describe two such electrodes. Use of such electrodes saves the user the step of manually applying the gel to the electrode at the time of electrode application and speeds the application process considerably. Thus, the ideal electrode would be one pre-gelled with high salt content conductive gel. Such an electrode would minimize application time by reducing the amount of skin "prepping" (abrasion) required by low salt content gels and eliminating the step of dispensing the gel onto the electrode surface.

Numerous prior art references exist that show that one can make a pregelled electrode by chloriding the surface of a silver substrate to create a Ag/AgCl electrode element with a stable half cell potential. Often, a silver-plated plastic substrate is used instead of solid silver, for cost reasons. An electrolytic gel may then be applied at the time of manufacture to create a pre-gelled electrode.

It is common in the art to construct single-piece sensors which incorporate multiple electrode elements on a single substrate. Such sensors have the advantages of low cost, ease of use, and precise positioning of the electrode elements. A common method of construction, as described in U.S. Pat. No. 5,337,748 issued to McAdams, utilizes a flexible circuit, created by printing a circuit on a plastic substrate using conductive ink. The conductive ink makes up the electrode sensing element and provides an electrical connection between the individual electrode elements and a cable connector, which facilitates connection to a data acquisition system. The conductive ink generally consists of flakes of silver (Ag) in a liquid binder. U.S. Pat. No. 4,852,572 issued to Nakahashi describes a pregelled, multiple electrode sensor constructed by printing a single layer of conductive ink on a non-woven cloth substrate. It is not possible, however, to pre-gel sensors constructed using conductive inks with liquid conductive gels because the salt content of the liquid gel quickly reacts with the Ag flakes in the ink and renders the circuit non-conductive. Such a process would lead to early sensor failure and a reduced shelf life. For this reason, sensors constructed using conductive inks are pre-gelled using a cured solid hydrogel with a low salt concentration. The use of a low salt content gel slows the rate at which the salt content of the gel corrodes the Ag element and therefore extends product shelf life. The impedance of the skin-electrode interface is generally higher than that which could be achieved with a high salt content gel, and the resultant electrical signal is much noisier. In addition, vigorous skin prepping is required to lower the impedance to an acceptable level, due to the limited hydrating properties of a solid gel.

Various prior art constructions exist which use multiple layers of conductive inks for low fidelity applications, such as the acquisition of resting EKG signals. One such construction is the TCP-3208 conductive coated polyester manufactured by Tolas Healthcare Packaging which includes a layer of conductive carbon material underneath a layer of conductive Ag/AgCl. The main purpose of this construction is to minimize the amount of silver (Ag) on a circuit trace, thus reducing the manufacturing cost. Such a construction generally makes use of solid hydrogel as the ionic interfacing material.

Another prior art construction, which is described in U.S. Pat. No. 5,337,748 issued to McAdams includes a single layer of Ag or Ag/AgCl ink on a flexible substrate such as vinyl or Melinex to make an electrode. Again, a solid hydrogel or a low concentration of salt in the liquid gel must be used in order to obtain an acceptable shelf life. Carrier in U.S. Pat. No. 5,352,315, teaches the use of a single conductive ink layer of either Ag/AgCl or a homogenous mixture of Ag/AgCl and carbon inks printed on a nonconductive backing layer.

U.S. Pat. No. 4,787,390 issued to Takata teaches the use of snap and eyelet type construction, though in this case the snap and eyelet is simply used to make mechanical contact between different components of the electrode and not to provide a pressure-sealed gel isolation function. U.S. Pat. No. 4,444,194 issued to Burcham and U.S. Pat. No. 4,617,935 issued to Cartmell also teach the use of a snap and eyelet construction, but only for the purpose of physically connecting electrode components.

It is therefore a principal object of the present invention to provide an electrophysiological electrode that utilizes a flexible circuit construction while allowing for the use of high salt content liquid electrolytic gels.

Another object of the present invention is to provide an electrophysiological electrode that contains a single interfacing contact to an electrophysiological monitor or other data acquisition system.

It is a further object of the present invention to provide an electrophysiological electrode with pre-gelled electrodes which provide low impedance while reducing the need for skin preparation.

SUMMARY OF THE INVENTION

This invention is an electrophysiological electrode that includes multiple layers of materials to isolate liquid electrolytic gels from the conductive inks on the flexible circuit of the electrode substrate. Such an electrode has a much longer shelf life under normal storage conditions than other electrodes of such construction with high salt content liquid electrolytic gel, and is able to maintain acceptable impedance upon its eventual use.

These and other objects and features of the present invention will be more fully understood from the following detailed description which should be read in light of the accompanying drawings in which corresponding reference numerals refer to corresponding parts throughout the several views.

DETAILED DESCRIPTION OF THE PREFERRED EMBODIMENT

Figure 1:
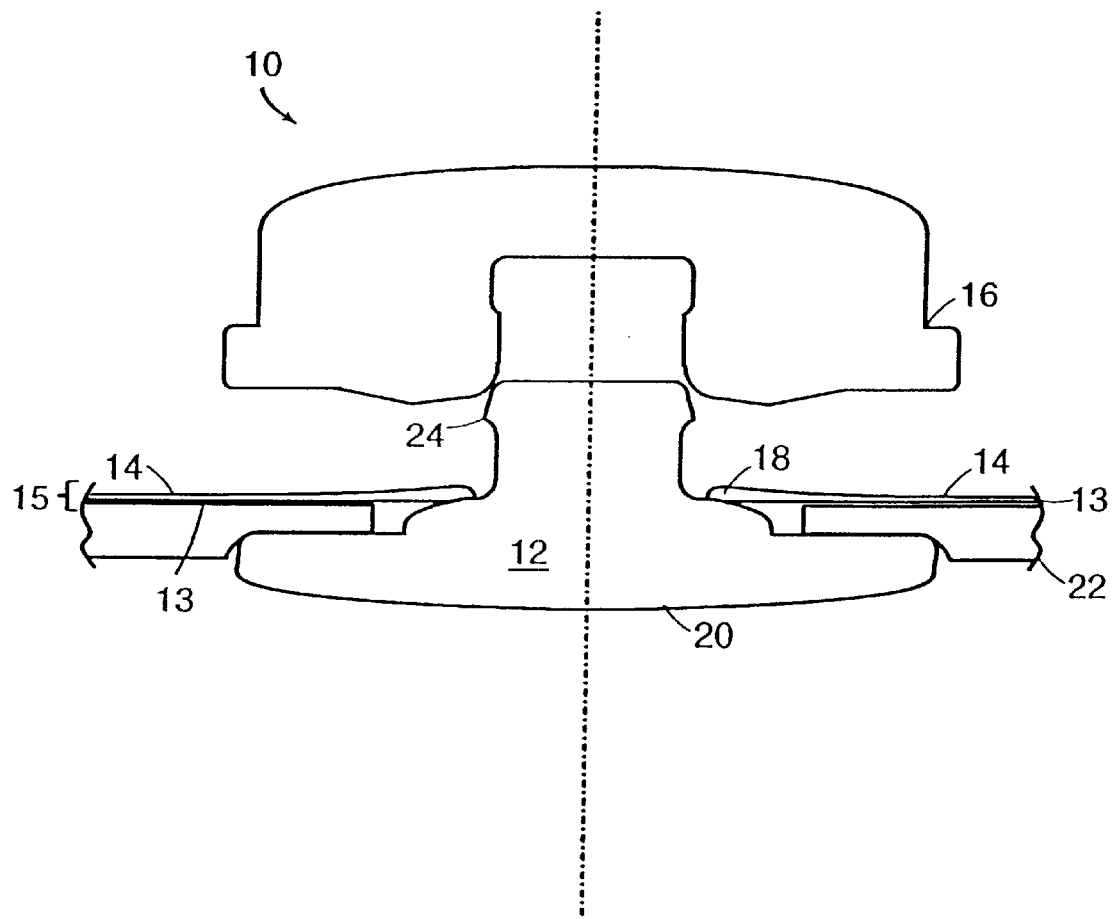
FIG. 1 is a side elevational view of a preferred embodiment of an electrode of the present invention which uses a snap and eyelet assembly press fit onto a flexible circuit for electrical contact and a foam material for liquid seal.
Figure 2A:
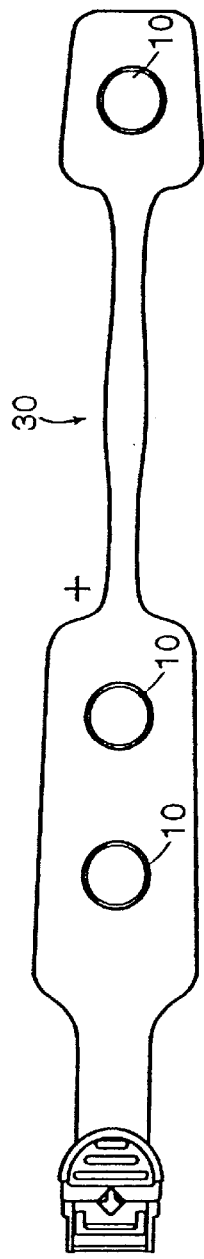
FIG. 2(a) is a top plan view of a sensor incorporating the electrodes shown in FIG. 1.
Figure 2B:
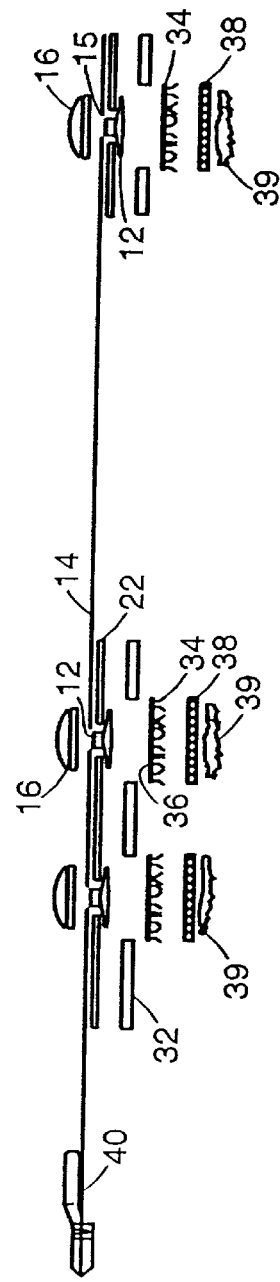
FIG. 2(b) is a side elevational view of the sensor shown in FIG. 2(a) which shows the snap and eyelet function of making electrical contact and liquid sealing.
Figure 3:
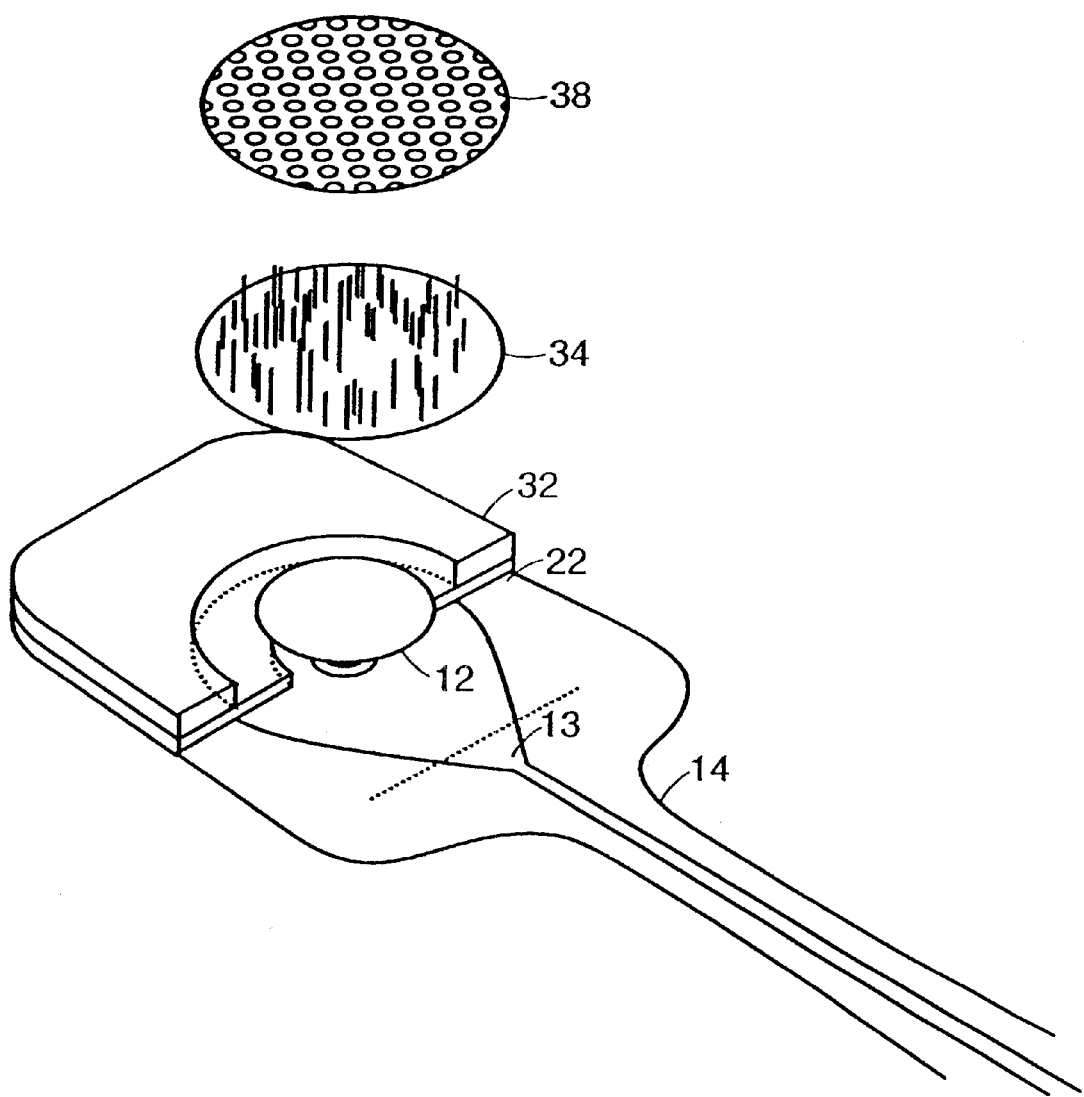
FIG. 3 is an exploded perspective view of the embodiment of a sensor of the present invention shown in FIGS. 1, 2(a) and 2(b) in which the foam materials are partially cut away.

Referring to FIGS. 1–3, a preferred embodiment of an electrode 10 of the present invention is shown which makes use of a conductive Ag/AgCl-plated ABS (acrylo-nitrile butadiene styrene) plastic eyelet 12 attached to a flexible polyester substrate 14 by means of a pressure-fitted non-conductive plastic snap 16. A conductive trace 13 is printed on the underside of the flexible substrate 14 with Ag conductive ink such as Dupont 5000 screen printable ink, producing a flexible circuit 15. This flexible circuit makes electrical contact with the eyelet 12 at the eyelet shoulder 18. The bottom 20 of the eyelet 12 is in contact with the liquid gel 39 (see FIG. 2(b)). The eyelet bottom 20 is physically isolated from its shoulder 18 by a layer of foam 22 with a punched hole for the eyelet shoulder 18 and top 24 to pass through. The foam 22 prevents the liquid gel from coming into contact with the conductive Ag ink of the flexible circuit. In the preferred embodiment, the foam is 1/32" thick double-sided adhesive-backed polyethylene foam, an example of which is sold by MACTAC. The preferred diameter of the punched foam hole is 0.050" larger than the shoulder diameter. The preferred eyelet shoulder diameter is 0.22" and the preferred foam hole diameter is 0.27 inches.

In a preferred embodiment shown in FIG. 2, the snap and eyelet assembly is integrated into a multiple electrode element sensor 30. FIG. 2 also more clearly shows the additional components of a multiple element sensor constructed using multiple snap and eyelet electrode assemblies 10.

In the preferred embodiment shown in FIG. 2(b), the plastic snap 16 is pressed down over the top of the eyelet 12, sandwiching the flexible circuit 15 and the foam seal layer 22 between the eyelet 12 and the snap 16. A basepad layer 32 of 1/16" double-sided adhesive foam is placed below the foam seal layer 22. As shown most clearly in FIG. 3, the top side of the basepad layer 32 (shown with a portion cut away) adheres firmly to the from of the seal layer 22 and it contains a circular hole of 0.6" diameter concentric to the eyelet creating a cylindrical housing to contain the liquid gel. The foam of the basepad layer 32 is made of the same foam as that of the seal layer 22.

The preferred embodiment utilizes a studded, porous spacer made of a disc 34, 0.6 inches in diameter, stamped out of Velcro hook material. The hook material has been sheared to make tines that will serve as a skin prepping mechanism when the user presses against them during use, in the same manner as described in U.S. Pat. No. 5,305,746 issued to Fendrock and assigned to the assignee of the present application. The backing 36 of the Velcro material is porous. The preferred Velcro thickness (including backing and tine profile) is approximately 0.08 inches. The liquid gel 39 is held in the gel pocket by a porous sponge 38, which is a urethane open pore sponge in the preferred embodiment.

The pressure exerted by the snap fit between the snap 16 and the eyelet 12 provides constant electrical contact between the eyelet 12 and the conductive trace 13 of the flexible printed circuit 15 at the shoulder 18 of the eyelet 12.

The pressure fit assembly also sandwiches the foam seal layer 22 between the snap 16 and the eyelet 12. This gaskets the top area of the eyelet and produces a tight seal which keeps the liquid gel 39 from contacting the flexible circuit 15. As a result, the gel is confined to the gel pocket below the bottom surface of the eyelet 12 and is not allowed to come in contact with the conductive Ag ink on the flexible circuit. The preferred conductive liquid gel is 10% salt content liquid hydrogel.

The flexible circuit 15 is connected to a cable connector 40, which allows connection of the electrode to a data acquisition system (not shown).

Figure 4:
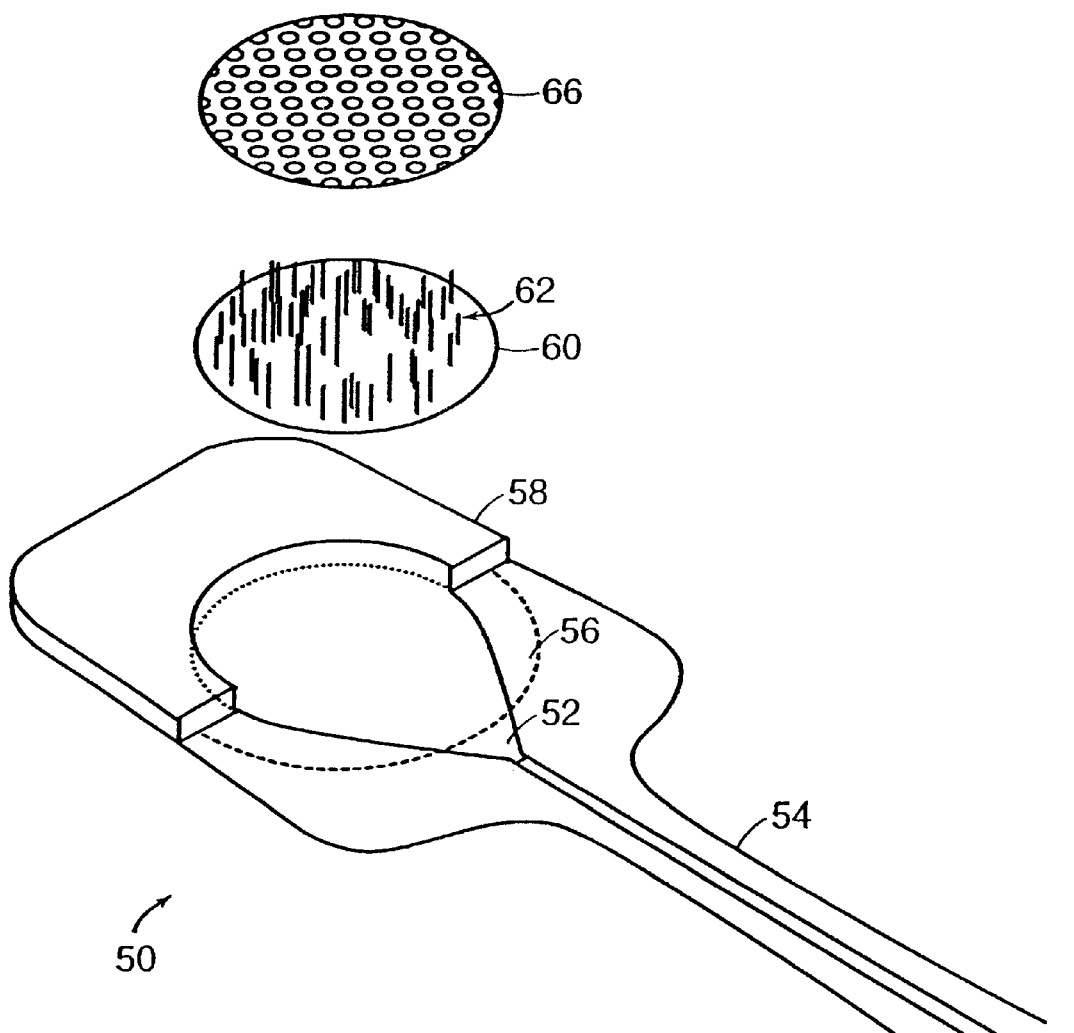
FIG. 4 is an exploded perspective view of another preferred embodiment of the present invention which uses two passes of ink and an electrolytic gel over the ink.
Figure 5A:
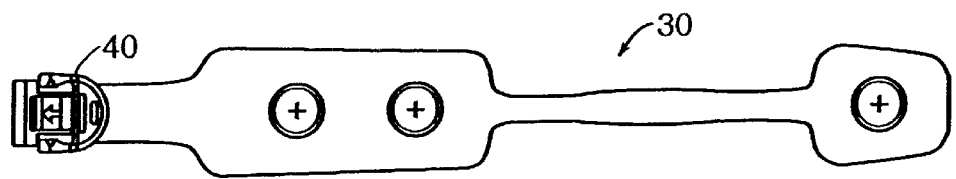
FIG. 5(a) is a top plan view of an alternate embodiment of a sensor of the present invention in which a Ag/AgCl screen is printed over Ag ink on a flexible substrate.
Figure 5B:
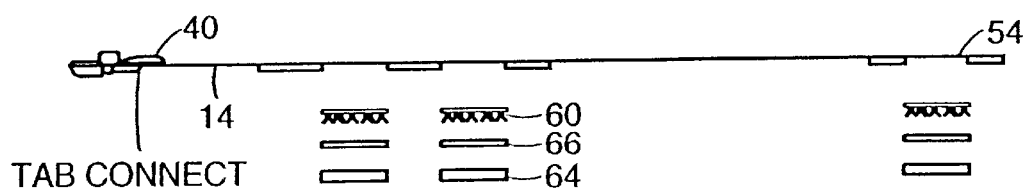
FIG. 5(b) is a side elevational view of the sensor shown in FIG. 4.

Another embodiment which accomplishes the goal of isolating the conductive Ag ink from the high salt content conductive gel is shown in FIGS. 4, 5(a) and 5(b). In this alternate embodiment, a flexible circuit 50 is created by printing a layer of conductive Ag ink 52 on a flexible plastic substrate (Mylar) 54. Isolation of the Ag conductor from the gel is accomplished by printing an eyelet layer 56 of Ag/AgCl ink (Acheson 7019™ in the preferred embodiment) over the conductive Ag ink 52. The eyelet layer 56 serves the same function as the eyelet 12 in the snap and eyelet embodiment shown in FIG. 1.

A basepad 58 (shown with a portion cut away) of 1/16" double-sided adhesive foam with a circular hole of 0.6" diameter, is placed onto the plastic substrate 54 so that the hole is centered concentric to the eyelet. This hole in the basepad 58 creates a cylindrical housing which is used to contain the liquid gel. Additionally, there is a studded, porous spacer disc 60, 0.6 inches in diameter, stamped out of Velcro hook material. The hooks 62 on the disc 60 have been sheared to make tines that will serve as a skin prepping mechanism when the user presses against them during use. The backing of the disc 60 is porous to allow the gel to go through it and provides full conductivity in the direction perpendicular to the electrode substrate. The preferred Velcro thickness including the tine profile is approximately 0.08 inches. The liquid gel is held in the cylindrical housing by a porous spacer sponge 66 made out of urethane porous material which is impregnated with the liquid gel.

The flexible printed conductive circuit 50 electrically connects the electrode element to a cable connector 40 (FIG. 5(a)). The cable connector allows connection of the sensor to a data acquisition system.

Placing a layer of chlorided material over the non-chlorided conductive material as described above provides the following benefits over prior art:
The Ag/AgCl surface serves the same purpose of the eyelet in the embodiment shown in FIG. 1, electrically interfacing to the conductive gel. It also provides a limited isolation of the conductive Ag layer from the corrosive effects of the conductive gel. The isolation is limited because the screen printing process creates a porous Ag/AgCl surface that is not completely impermeable.

Because AgCl is not initially present in the bottom layer, any increase in AgCl in the Ag layer resulting from chloriding reactions which occur between the conductive gel and the metal (Ag) flakes in the conductive ink will cause the concentration of AgCl in the Ag layer to increase from zero rather than from an initial concentration greater than zero. This extends the life of the product by providing more Ag flakes at the start which translates to more conductive paths. In addition, because there are no large molecules of AgCl in the underlying conductive layer, the Ag flakes are closely bound together and prevent the electrolyte from penetrating any large gaps left unfilled by the binding substrate of the ink. This slows down the chloriding process. In addition, the Ag flakes are closely bound together and thus maintain a higher conductivity than a Ag/AgCl ink. This translates to less noise overall during data collection.

Other alternate embodiments utilize carbon, nickel, copper or other metal inks on the bottom layer instead of silver for electrodes that do not require high noise sensitivity.

Another alternate embodiment utilizes solid instead of liquid hydrogels. While solid hydrogels have lower conductivities than liquid gels, their use can be advantageous for sensors which incorporate closely-spaced multiple electrode sensors. In such an application, the higher material crosslinking of the solid hydrogel prevents shorting of the electrode elements due to gel migration, which would occur if liquid gels were used. This embodiment allows the use of solid hydrogels with higher salt content than is commonly used while still achieving the same intent to maximize shelf life.

Figure 6:
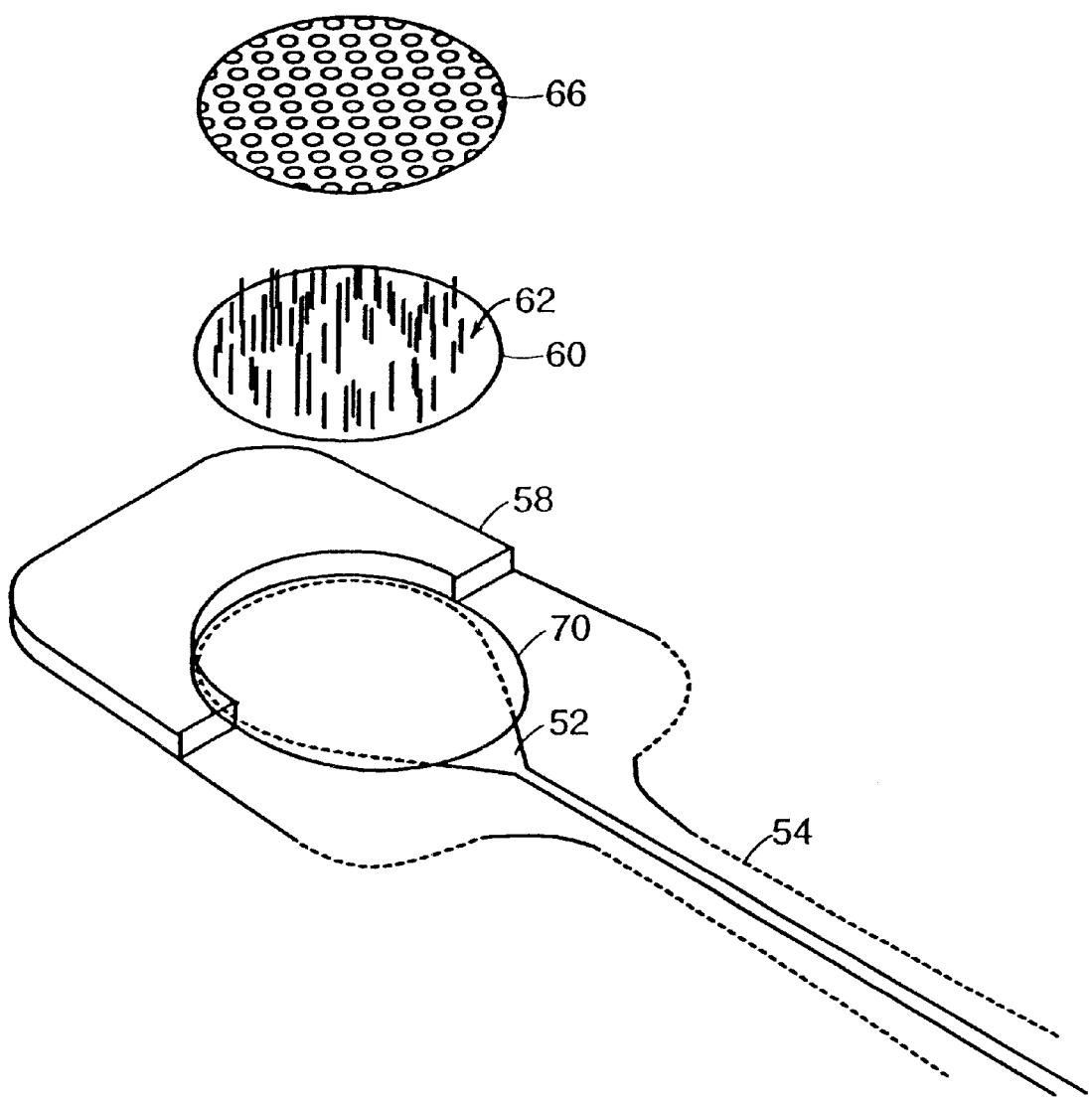
FIG. 6 is an exploded perspective view of another preferred embodiment of the electrode of the present invention.

The embodiment of the electrode of the present invention shown in FIG. 6 utilizes a layer of solid hydrogel 70 as a barrier layer between the conductive ink 52 and the liquid gel impregnated in the sponge 66. This construction uses an Ag/AgCl conductive ink and the layer of solid hydrogel 70 acts as an exchange barrier between the conductive ink 52 and the liquid gel.

While the foregoing invention has been described with reference to its preferred embodiments, various alterations and modifications will occur to those skilled in the art. For example, while various dimensions are recited above for components of the present invention, it should be understood that these are simply the preferred dimensions and that differently sized components could be used and different number of electrodes could be incorporated on a sensor and still achieve the intended results. These and all other such alterations and modifications are intended to fall within the scope of the appended claims.

What is claimed is:

1. An electrode for measuring electrophysiological signals, the electrode comprising:
    a substrate of flexible non-conductive non-metallic material;
    a conductive metal ink layer deposited on said substrate;
    a physically distinct barrier layer of silver/silver chloride (AG/AgCl) deposited over and contiguous with said conductive metal ink layer,
    predispensed salt content based conductive gel;
    wherein said barrier layer isolates said conductive ink layer from said conductive gel.

2. The electrode of claim 1 wherein said barrier layer comprises a component plated with Ag/AgCl material.

3. The electrode of claim 1 wherein said barrier layer comprises a screen printed ink layer of Ag/AgCl material.

4. The electrode of claim 1 wherein said barrier layer comprises a flexo-printed ink layer of Ag/AgCl material.

5. The electrode of claim 1 wherein said conductive metal ink layer is silver (Ag).

6. The electrode of claim 1 wherein said conductive gel is a liquid electrolytic gel.

7. The electrode of claim 1 wherein said conductive gel is a solid hydrogel gel.

8. The electrode of claim 1 wherein printed graphics are printed on a side of said flexible substrate opposite the side where said conductive metal ink layer is located.

9. An electrode for measuring electrophysiological signals, the electrode comprising:
    a conductive gel;
    a substrate of flexible non-conductive material;
    a conductive ink circuit printed on said substrate;
    a barrier layer of conductive material placed between said conductive ink circuit and said gel;
    a ring or pad of nonconductive material positioned between a surface of said flexible substrate bearing a conductive ink circuit and said barrier layer of conductive material, said ring or pad of nonconductive material extending from the outer edge of the barrier layer of conductive material to an extent sufficient to act as an isolating gasket to completely separate the conductive ink circuit from the conductive gel.

10. An electrode for measuring electrophysiological signals, the electrode comprising:
    a conductive gel;
    a substrate of flexible non-conductive material;
    a conductive ink circuit printed on said substrate;
    a barrier layer of conductive material placed between said conductive ink circuit and said gel, said barrier layer being a solid hydrogel.

11. The electrode of claim 9 wherein said nonconductive material is a transfer film.

12. The electrode of claim 9 wherein said nonconductive material is a double coated adhesive foam backing.

13. The electrode of claim 9 wherein said barrier layer of conductive material is secured to said ring or pad of nonconductive material and to said flexible substrate bearing a conductive ink circuit by means of a snap or ring that is pressure fit to such barrier layer.

14. The electrode of claim 9 wherein said conductive ink circuit is made of carbon ink.

15. The electrode of claim 9 wherein said barrier layer of conductive material is a layer of Ag/AgCl.

* * * * *